(12) United States Patent
Van Nguyen et al.

(10) Patent No.: US 7,468,180 B2
(45) Date of Patent: Dec. 23, 2008

(54) COMPOSITIONS COMPRISING AT LEAST ONE HYDROXIDE COMPOUND AND AT LEAST ONE OXIDIZING AGENT, AND METHODS TO STRAIGHTEN CURLY HAIR

(75) Inventors: Nghi Van Nguyen, Edison, NJ (US); David W. Cannell, Plainfield, NJ (US)

(73) Assignee: L'Oreal, S.A., Paris (FR)

(*) Notice: Subject to any disclaimer, the term of this patent is extended or adjusted under 35 U.S.C. 154(b) by 765 days.

(21) Appl. No.: 09/931,913

(22) Filed: Aug. 20, 2001

(65) Prior Publication Data

US 2003/0037384 A1 Feb. 27, 2003

(51) Int. Cl.
*A61Q 5/00* (2006.01)
(52) U.S. Cl. ............... 424/70.1; 424/70.4; 424/70.6; 424/70.12; 424/70.11; 424/70.14; 424/70.22; 424/70.23
(58) Field of Classification Search ............ 424/70.2, 424/70.4, 70.6, 70.12, 70.122, 70.14, 70.22, 424/70.23, 70.112, 70.1
See application file for complete search history.

(56) References Cited

U.S. PATENT DOCUMENTS

| | | | |
|---|---|---|---|
| 2,405,166 A | 8/1946 | Reed et al. | |
| 2,464,280 A | 3/1949 | Reed et al. | |
| 2,464,281 A | 3/1949 | Peterson | |
| 2,564,722 A | 8/1951 | Reed et al. | |
| 2,719,814 A | 10/1955 | Haefele | |
| 3,017,328 A | 1/1962 | Childrey, Jr. et al. | |
| 3,066,077 A | 11/1962 | De Mytt et al. | |
| 3,242,052 A | 3/1966 | Sheffner | |
| 3,243,346 A | 3/1966 | Bechmann et al. | |
| 3,252,866 A | 5/1966 | Sheffner | |
| 3,533,417 A | 10/1970 | Bartoszewicz et al. | |
| 3,654,936 A | 4/1972 | Wajaroff | |
| 3,908,672 A | 9/1975 | Bore et al. | 132/7 |
| 3,971,391 A | 7/1976 | Bore et al. | 132/7 |
| 3,973,574 A | 8/1976 | Minagawa, et al. | 132/7 |
| 4,139,610 A | 2/1979 | Miyazaki et al. | |
| 4,153,681 A | 5/1979 | Shiba | |
| 4,175,572 A | 11/1979 | Hsiung et al. | |
| 4,218,435 A | 8/1980 | Shiba | |
| 4,237,910 A | 12/1980 | Khahil et al. | 132/7 |
| 4,272,517 A | 6/1981 | Yoneda et al. | |
| 4,303,085 A | 12/1981 | de la Guardia et al. | |
| 4,304,244 A | 12/1981 | de la Guardia | |
| 4,314,572 A | 2/1982 | de la Guardia et al. | |
| 4,322,401 A | 3/1982 | Harada | |
| 4,324,263 A | 4/1982 | de la Guardia | |
| 4,361,157 A | 11/1982 | James | |
| 4,373,540 A | 2/1983 | de la Guardia | |
| 4,390,033 A | 6/1983 | Khalil et al. | |
| 4,416,296 A | 11/1983 | Meyers | |
| 4,424,820 A | 1/1984 | Cannell et al. | 132/7 |
| 4,509,983 A | 4/1985 | Szabó et al. | |
| 4,605,018 A | 8/1986 | de la Guardia et al. | |
| 4,783,395 A | 11/1988 | Hsieh et al. | |
| 4,793,994 A | 12/1988 | Helioff et al. | |
| 4,816,246 A | 3/1989 | Mathews et al. | 424/72 |
| 4,859,459 A | 8/1989 | Greiche et al. | 424/71 |
| 4,895,722 A | 1/1990 | Abe et al. | |
| 4,898,726 A | 2/1990 | Beste | |
| 4,950,485 A | 8/1990 | Akhtar et al. | |
| 4,956,175 A | 9/1990 | Maignan et al. | |
| 4,992,267 A | 2/1991 | DenBeste et al. | 427/71 |
| 5,015,767 A | 5/1991 | Maignan et al. | |
| 5,077,042 A | 12/1991 | Darkwa et al. | |
| 5,106,612 A | 4/1992 | Maignan et al. | |
| 5,154,918 A | 10/1992 | Maignan et al. | |
| 5,223,252 A | 6/1993 | Kolc et al. | |
| 5,294,230 A | 3/1994 | Wu et al. | |
| 5,332,471 A | 7/1994 | Naddeo et al. | 162/6 |
| 5,332,570 A | 7/1994 | Bergstrom et al. | |
| 5,348,737 A | 9/1994 | Syed et al. | |
| 5,376,364 A | 12/1994 | Darkwa et al. | |
| 5,419,895 A | 5/1995 | Kubo et al. | |
| 5,523,078 A | 6/1996 | Baylin | |
| 5,565,192 A | 10/1996 | Leroy et al. | |
| 5,565,216 A | 10/1996 | Cowsar et al. | |
| 5,591,425 A | 1/1997 | Dhaliwal | 424/70.4 |
| 5,609,859 A | 3/1997 | Cowsar | |

(Continued)

FOREIGN PATENT DOCUMENTS

CN 1138450 12/1996

(Continued)

OTHER PUBLICATIONS

S. Ogawa et al. A curing method for permanent hair straightening using thioglycolic and dithiodiglycolic acids, *Journal of Cosmetic Science*, 51, 379-399 (Nov./Dec. 2000).

(Continued)

*Primary Examiner*—Eisa B Elhilo
(74) *Attorney, Agent, or Firm*—Finnegan, Henderson, Farabow, Garrett & Dunner, LLP

(57) ABSTRACT

Compositions, optionally heat-activated, methods and kits for lanthionizing keratinous fibers to achieve relaxation of the keratinous fibers comprising applying to keratinous fibers a composition comprising at least one hydroxide compound and at least one oxidizing agent.

44 Claims, No Drawings

U.S. PATENT DOCUMENTS

| | | | |
|---|---|---|---|
| 5,628,991 | A | 5/1997 | Samain et al. |
| 5,637,295 | A | 6/1997 | Lang et al. |
| 5,641,477 | A | 6/1997 | Syed et al. |
| 5,679,327 | A | 10/1997 | Darkwa et al. |
| 5,679,332 | A | 10/1997 | Braun et al. |
| 5,725,848 | A | 3/1998 | Borish et al. ............... 424/70.5 |
| 5,753,215 | A | 5/1998 | Mougin et al. |
| 5,775,342 | A | 7/1998 | Hoenstein et al. ........... 132/204 |
| 5,824,295 | A | 10/1998 | Syed et al. |
| 5,849,277 | A | 12/1998 | Cowsar |
| 5,932,201 | A | 8/1999 | de Labbey et al. |
| 5,935,558 | A | 8/1999 | Malle |
| 5,961,667 | A | 10/1999 | Doehling et al. |
| 6,058,943 | A | 5/2000 | Davis-Harris ............... 132/205 |
| 6,287,582 | B1 | 9/2001 | Gott et al. |
| 6,435,193 | B1 | 8/2002 | Cannell et al. |
| 6,782,895 | B2 | 8/2004 | Van Nguyen et al. |
| 6,792,954 | B2 | 9/2004 | Cannell et al. |
| 2002/0189027 | A1 | 12/2002 | Cannell et al. |

FOREIGN PATENT DOCUMENTS

| | | |
|---|---|---|
| DE | 28 23 243 | 11/1979 |
| DE | 35 19 463 A1 | 12/1986 |
| DE | 43 26 974 A1 | 5/1994 |
| EP | 0 354 835 A1 | 2/1990 |
| EP | 0 465 342 A1 | 1/1992 |
| EP | 0 512 879 A2 | 11/1992 |
| EP | 0 636 358 A1 | 2/1995 |
| EP | 0 667 141 A2 | 8/1995 |
| EP | 0 712 623 | 5/1996 |
| EP | 0 714 654 A1 | 6/1996 |
| EP | 0 726 251 A1 | 8/1996 |
| GB | 1002889 | 9/1965 |
| GB | 1 281 662 | 7/1972 |
| JP | A S50-029756 | 3/1975 |
| JP | A S50-029757 | 3/1975 |
| JP | 51 9013 | 3/1976 |
| JP | A S63-190814 | 8/1988 |
| JP | A H02-104515 | 4/1990 |
| JP | A H04-243860 | 8/1992 |
| JP | A H04-295413 | 10/1992 |
| JP | A H5-39211 | 2/1993 |
| JP | A H05-246827 | 9/1993 |
| JP | A H6-172141 | 6/1994 |
| JP | A H6-343511 | 12/1994 |
| JP | A H7-101840 | 4/1995 |
| JP | A H08-245559 | 9/1996 |
| JP | A 2002-003346 | 1/2002 |
| JP | A 2002-68976 | 3/2002 |
| WO | WO 87/05500 | 9/1987 |
| WO | WO 89/06122 A | 7/1989 |
| WO | WO 93/01791 A | 2/1993 |
| WO | WO 97/07775 | 3/1997 |
| WO | WO 99/18922 | 4/1999 |
| WO | WO 01/64171 A2 | 9/2001 |
| WO | WO 01/74318 A2 | 10/2001 |

OTHER PUBLICATIONS

Co-pending U.S. Appl. No. 09/789,667—Title: Hair Relaxer Compositions Comprising at Least One Hydroxide Compound and at Least One Activating Agent, and Methods of Using the Same Inventors: David W. Cannell et al. U.S. Filing Date: Feb. 22, 2001.
Co-pending U.S. Appl. No. 09/516,942—Title: Hair Relaxer Compositions Utilizing Complexing Agent Activators Inventors: Nghi Van Nguyen et al. U.S. Filing Date: Mar. 1, 2000.
Co-pending U.S. Appl. No. 09/931,919—Title: Method for Relaxing and Re-Waving Hair Comprising at Least One Reducing Agent And at Least One Hydroxide Compound Inventors: David W. Cannell et al. U.S. Filing Date: Apr. 20, 2001.
Co-pending U.S. Appl. No. 09/838,197—Title: Composition and Methods for Lanthionizing Keratin Fibers Using at Least One Organic Nucleophile and at Least One Hydroxide Ion Generator Inventors: David W. Cannell et al. U.S. Filing Date: Apr. 20, 2001.
Co-pending U.S. Appl. No. 09/717,206—Title: Hair Relaxer Compositions Utilizing Cation Exchange Compositions Inventors: David W. Cannell et al. U.S. Filing Date: Nov. 22, 2001.
Co-pending U.S. Appl. No. 09/931,914—Title: Compositions Comprising at Least One Hydroxide Compound and at Least One Complexing Agent, and Methods for Using the Same Inventors: Nghi Van Nguyen et al. U.S. Filing Date: Aug. 20, 2001.
Co-pending U.S. Appl. No. 09/931,912—Title: Compositions Comprising at Least One Hydroxide Compound and at Least One Reducing Agent, and Methods for Relaxing Inventors: Nghi Van Nguyen et al. U.S. Filing Date: Aug. 20, 2001.
International Search Report in PCT/US02/21848 dated Nov. 25, 2002.
Advisory Action dated Jul. 22, 2005, in co-pending U.S. Appl. No. 09/789,667.
English language Derwent Abstract for CN 1138450 (Dec. 1996).
English language Derwent Abstract for JP-A 2002-003346 (Jan. 2002).
English language Derwent Abstract for JP-A 2002-68976 (Mar. 2002).
English language Derwent Abstract for JP-A H6-172141 (Jun. 1994).
English language Derwent Abstract for JP-A H7-101840 (Apr. 1995).
Hair Science: Japan Hair Science Assoc., Jan. 10, 1996, 2nd. Ed., p. 87.
BASF Corporation on-line catalog http://www.basf.com/businesses/consumer/cosmeticingredients/pdfs/ethnic_haircare.pdf.
Clariant, "Tylose Water-soluble cellulose ethers", Product range and fields of Application.
Co-pending U.S. Appl. No. 10/214,942—Title: Hair Relaxer Compositions Utilizing Cation Exchange Composition.
English language Derwent Abstract for DE 28 23 243 (Nov. 1979).
English language Derwent Abstract for DE 35 19 463 (Dec. 1986).
English language Derwent Abstract for DE 43 26 974 (May 1994).
English language Derwent Abstract for EP 0 465 342 (Jan. 1992).
English language Derwent Abstract for JP 60021704 (Apr. 1985).
English language Derwent Abstract for JP 76-09013 (Mar. 1976).
Examiner's Answer dated Jun. 14, 2005, in co-pending U.S. Appl. No. 09/838,197.
International Search Report for International Appl. No. PCT/US01/43193 Jul. 5, 2002.
International Search Report for International Application No. PCT/US02/03392, May 8, 2002.
International Search Report for International Application No. PCT/US02/08270, Aug. 7, 2002.
International Search Report for International Application No. PCT/US02/21846, Nov. 8, 2002.
International Search Report for International Application No. PCT/US02/21849, May 25, 2003.
Office Action dated Apr. 28, 2003, in co-pending U.S. Appl. No. 09/931,914 (issued as U.S. Patent No. 6,782,895).
Office Action dated Apr. 12, 2005, in co-pending U.S. Appl. No. 09/789,667.
Office Action dated Aug. 6, 2003, in co-pending U.S. Appl. No. 09/838,197.
Office Action dated Dec. 16, 2003, in co-pending U.S. Appl. No. 10/214,942 (Now issued as U.S. Patent No. 6,792,954).
Office Action dated Feb. 6, 2003, in co-pending U.S. Appl. No. 09/838,197.
Office Action dated Feb. 5, 2003, in co-pending U.S. Appl. No. 09/789,667.
Office Action dated Jul. 22, 2004, in co-pending U.S. Appl. No. 09/838,197.
Office Action dated Jul. 26, 2004, in co-pending U.S. Appl. No. 09/789,667.
Office Action dated Jul. 31, 2003, in co-pending U.S. Appl. No. 09/789,667.
Office Action dated Mar. 8, 2005, in co-pending U.S. Appl. No. 09/931,912.

Office Action dated May 24, 2004, in co-pending U.S. Appl. No. 09/931,912.

Office Action dated Oct. 27, 2003 in co-pending U.S. Appl. No. 09/931,912.

Office Action dated Sep. 9, 2003, in co-pending U.S. Appl. No. 09/931,914 (issued as U.S. Patent No. 6,782,895).

Office Action dated Sep. 10, 2002, in co-pending U.S. Appl. No. 09/789,667.

Robbins, Clarence R., "Chemical and physical behavior of human hair," pp. 124-126, 148-151, and 162-163, Springer (2002).

Schoon, Douglas D., "Hair structure and chemistry simplified", Revised edition, pp. 191-192, Milady Publishing Co. (1993).

Zahn, Helmut, "N, O-Peptidyl shift, disulfide exchange, and lanthionine formation in wool and other proteins containing cystine," Chimia (Switz.) (1961), 15, 378-94.

Zviak, C., The Science of Hair Care, pp. 185-186 (1986).

COMPOSITIONS COMPRISING AT LEAST ONE HYDROXIDE COMPOUND AND AT LEAST ONE OXIDIZING AGENT, AND METHODS TO STRAIGHTEN CURLY HAIR

FIELD OF THE INVENTION

The present invention relates to compositions, kits comprising these compositions, and methods for using these compositions for lanthionizing keratinous fibers to achieve relaxation of the keratinous fibers using a combination of at least one hydroxide compound and at least one oxidizing agent.

BACKGROUND OF THE INVENTION

Straightening or relaxing the curls of very curly hair may increase the manageability and ease of styling of such hair. In today's market, there is an increasing demand for the hair care products referred to as "hair relaxers," which can relax or straighten naturally curly or kinky hair. Hair relaxers may either be applied in a hair salon by a professional or in the home by the individual consumer.

Hair fiber, a keratinous material, comprises proteins (polypeptides). Many of the polypeptides in hair fibers are bonded together or cross-linked with disulfide bonds (—S—S—). A disulfide bond may be formed from the reaction of two sulfhydryl groups (—SH), one on each of two cysteine residues, which results in the formation of a cystine residue. A cystine residue comprises a cross-link of the formula —CH$_2$—S—S—CH$_2$— between 2 polypeptides. While there are other types of bonds which occur between the polypeptides in hair fibers, such as ionic (salt) bonds, the permanent curling or the shape of the hair is essentially dependent on the disulfide bonds of cystine residues.

Generally, hair relaxing processes are chemical processes which may alter the aforementioned disulfide bonds between polypeptides in hair fibers and may form lanthionine residues [S[CH$_2$CH(NH—)(CO—)]$_2$]. Thus, the term "lanthionizing" is used when one skilled in the art refers to the relaxing of keratin fibers by hydroxide ions. "Lanthionizing," as used herein, refers to the formation of at least one lanthionine residue, which may accomplish, for example, any level of relaxation. "Relaxation" and "relaxing," as used herein, includes any level of relaxing, for example, from slight relaxing to straightening.

For example, hair fibers may be relaxed or straightened by disrupting the disulfide bonds of the hair fibers with an alkaline reducing agent. The chemical disruption of disulfide bonds with such an agent is generally combined with mechanical straightening of the hair, such as combing, and straightening generally occurs due to changes in the relative positions of neighboring polypeptide chains within the hair fiber. This reaction is generally terminated by rinsing and/or application of a neutralizing composition.

The reaction with the alkaline agent is normally initiated by available hydroxide ions. As used herein, "available hydroxide ions" are hydroxide ions which are available for lanthionization. Not to be limited by theory, there are two reaction sequences that are predominantly used in the art to explain the disruption of the disulfide bonds in hair fibers by available hydroxide ions. Both of these reaction sequences result in lanthionine residue formation. Generally, hydroxide ions initiate a reaction in which a cystine cross-link (—CH$_2$—S—S—CH$_2$—) is broken and a lanthionine cross-link (—CH$_2$—S—CH$_2$—) is formed. The lanthionine cross-link is shorter than a cystine cross-link by one sulfur atom, and thus the net effect of the reaction is to reduce the distance between polypeptides. Amino acid analysis indicates that from 25 mole % to 40 mole % of cystine residues are converted to lanthionine residues.

One reaction sequence comprises at least one bimolecular nucleophilic substitution reaction wherein an available hydroxide ion directly attacks the disulfide linkage of a cystine residue. The result is the formation of lanthionine residues and HOS$^-$. See Zviak, C., *The Science of Hair Care*, pp. 185-186 (1986). The second reaction sequence comprises at least one β-elimination reaction initiated by the nucleophilic attack of an available hydroxide ion on a hydrogen atom bonded to a carbon atom that is in the p-position with respect to the disulfide bond of a cystine residue. Id. The result is the formation of a dehydroalanine residue which comprises a reactive double bond (=CH$_2$). The double bond of the dehydroalanine residue can then react with the thiol group of a cysteine residue to form a lanthionine residue. These stable irreversible crosslinks in the treated hair make subsequent chemical re-linking of the polypeptides unnecessary. Thus, the only step that may be required following a straightening process using such hydroxide-containing alkaline agents is the removal of any excess alkaline solution to avoid or minimize damage to the hair protein or skin. If such a step is required, an acidic shampoo may be used to neutralize residual alkali and remove it from the hair and scalp.

Hydroxide-containing alkaline agents also have other advantages. For example, alkaline agents, such as sodium hydroxide and guanidine hydroxide, do not have a highly objectionable odor or cause such an odor on treating the hair. Further, hydroxide-based straighteners generally have relatively fast processing times and good straightening of naturally curly or kinky hair. Additionally, the achieved straightening effect is more durable; i.e., less likely to revert to a curly state after shampooing and exposure to the elements than is hair straightened with some other straighteners.

Despite these advantages, certain hydroxide-containing alkaline agents may have disadvantages. These disadvantages may be heightened when the hydroxide-containing alkaline agent is sodium hydroxide. Specifically, the causticity of sodium hydroxide can adversely affect the condition of the hair, for example, leaving it in a brittle state and harsh to the touch. Additionally, prolonged or unnecessary exposure of hair to such a strong alkali can weaken, break and dissolve the hair. The mechanical properties of hair that has been lanthionized using hydroxide ion generating compositions demonstrate that, while the hair may not be significantly weaker due to the reduction in space between polypeptides (and in fact may have a high yield force), the hair may have a lower elongation before breaking. This "brittleness" of high yield force coupled with low elongation and inherently weaker points (where the hair had natural twists) can lead to breakage during grooming. Further, in some instances, such a strong alkali can discolor the natural color of the hair. For example, the tone of natural brown hair may be reddened and natural white or grey hair may be yellowed. Further, the natural sheen of the hair may be delustered.

Most frequently, commercial relaxing compositions are in the form of gels or emulsions that contain varying proportions of strong water-soluble bases, such as sodium hydroxide (NaOH), or of compositions that contain slightly-soluble metal hydroxides, such as calcium hydroxide (Ca(OH)$_2$), which can be converted in situ to soluble bases, such as guanidine hydroxide. Traditionally, the two main hair relaxers used in the hair care industry for generating hydroxide ions are referred to as "lye" (lye=sodium hydroxide) relaxers and "no lye" relaxers.

The "lye" relaxers generally comprise sodium hydroxide in a concentration ranging from 1.5% to 2.5% by weight relative to the total weight of the composition (0.38M-0.63 M) depending on the carrier used, the condition of the hair fibers and the desired length of time for the relaxation process.

While "no lye" relaxers may not contain lye, they may, however, rely on the soluble hydroxides of inorganic metals, such as potassium hydroxide and lithium hydroxide. Other "no lye" relaxers may use hydroxide ions obtained, for example, from a slightly-soluble source, such as $Ca(OH)_2$. For example, the slightly soluble $Ca(OH)_2$ may be mixed with guanidine carbonate to form guanidine hydroxide, a soluble but unstable source of hydroxide, and insoluble calcium carbonate ($CaCO_3$). This reaction is driven to completion by the precipitation of $CaCO_3$ and is, in effect, substituting one insoluble calcium salt for a slightly soluble calcium salt. Because guanidine hydroxide is unstable, the components are stored separately until the time of their use.

Some strides have been made to improve the condition of sodium hydroxide-straightened hair by incorporating an auxiliary hair keratin disulfide reducing agent having a sulfhydryl functional group available and chosen from cysteine, homologs of cysteine, and water soluble derivatives of cysteine. See, for example, U.S. Pat. No. 4,992,267, the disclosure of which is incorporated herein by reference. This patent discloses the use of sodium hydroxide at concentrations of between about 1 weight percent to about 2.5 weight percent, preferably between about 1.5 weight percent and about 2.25 weight percent relative to the total concentration of the composition.

Further, co-pending U.S. patent application Ser. No. 09/789,667, the disclosure of which is incorporated herein by reference, discloses compositions, and methods for using these compositions, for lanthionizing keratinous fibers comprising at least one hydroxide compound with the proviso that the at least one hydroxide compound is not sodium hydroxide, lithium hydroxide or potassium hydroxide and at least one activating agent chosen from cysteine-based compounds. These compositions may make it possible to even further decrease the amount of the at least one hydroxide compound needed while maintaining good hair condition.

SUMMARY OF THE INVENTION

The present invention, in one embodiment, may relax or straighten keratinous fibers without substantial damage to the fibers but at the same time without reversion to the original curly state of the hair using compositions comprising low concentrations of at least one hydroxide compound.

DETAILED DESCRIPTION OF THE INVENTION.

Thus, the present invention, in one aspect, provides a composition for lanthionizing keratinous fibers to achieve relaxation of the keratinous fibers comprising (i) at least one hydroxide compound and (ii) at least one oxidizing agent, wherein the at least one hydroxide compound and the at least one oxidizing agent are present in a combined amount effective to relax the keratinous fibers. In one embodiment, the composition is heat-activated.

The present invention also provides compositions for lanthionizing keratinous fibers to achieve relaxation of the keratinous fibers comprising (i) at least one hydroxide compound and (ii) at least one oxidizing agent, wherein the at least one hydroxide compound is present in an amount such that the amount of hydroxide ion in the composition ranges from 0.01% to 2% by weight relative to the total weight of the composition. In another inventive composition, the amount of hydroxide ion ranges from 0.01% to 1%, and in yet another inventive composition, ranges from 0.01% to 0.5%. In certain embodiments, these compositions are heat-activated.

In another aspect of the invention, the present invention provides a method for lanthionizing keratinous fibers to achieve relaxation of the keratinous fibers comprising: (i) generating hydroxide ions in at least one solvent, wherein the step of generating comprises including at least one hydroxide compound and at least one oxidizing agent in the at least one solvent; (ii) applying a composition comprising the generated hydroxide ions to keratinous fibers for a sufficient period of time to lanthionize at least one keratinous fiber; and (iii) heating the keratinous fibers, wherein the at least one hydroxide compound and the at least one oxidizing agent are present in a combined amount effective to relax at least one of the keratinous fibers, further wherein the composition is applied prior to or during heating.

Further, the invention also provides for a multicompartment kit for lanthionizing keratinous fibers, wherein the kit comprises at least two compartments. A first compartment of the kit contains at least one hydroxide compound, and a second compartment contains at least one oxidizing agent.

Certain terms used herein are defined below:

As used herein, "at least one" means one or more and thus includes individual components as well as mixtures/combinations.

"Keratinous fibers" as defined herein may be human keratinous fibers, and may be chosen from, for example, hair.

"Heating" refers to the use of elevated temperature (i.e., above 100° C.). In one embodiment, the heating in the inventive method may be provided by directly contacting the keratinous fibers with a heat source, e.g., by heat styling of the keratinous fibers. Non-limiting examples of heat styling by direct contact with the keratinous fibers include flat ironing, and curling methods using elevated temperatures (such as, for example, curling with a curling iron and/or hot rollers). In another embodiment, the heating in the inventive method may be provided by heating the keratinous fibers with a heat source which may not directly contact the keratinous fibers. Non-limiting examples of heat sources which may not directly contact the keratinous fibers include blow dryers, hood dryers, heating caps and steamers.

"A heat-activated" composition, as used herein, refers to a composition which relaxes keratinous fibers better than the same composition which is not heated during or after application of the composition.

"High humidity" as defined herein refers to atmospheric humidity above 40%.

It is to be understood that both the foregoing general description and the following detailed description are exemplary and explanatory only and are not restrictive of the invention as claimed.

As described above, the lanthionization of keratinous fibers is believed to be driven by the disruption of the disulfide bonds of cystine residues in the fibers. The compositions and methods of the present invention may provide a novel way of generating sufficient available hydroxide ions from at least one hydroxide compound to effectively relax and/or straighten the hair with lower concentrations of the at least one hydroxide compound. Such compositions may, in one embodiment, be capable of relaxing the keratinous fibers without damaging the fibers. This is particularly true when the compounds are applied to the hair, and then the hair is heated.

Thus, the present invention provides, in one embodiment, a composition for lanthionizing keratinous fibers to achieve relaxation of the keratinous fibers comprising (i) at least one hydroxide compound and (ii) at least one oxidizing agent. The at least one hydroxide compound and the at least one oxidizing agent are present in a combined amount effective to relax keratinous fibers. In one embodiment, the composition is heat-activated. In one embodiment, the composition further comprises a cation exchange composition. In another embodiment, the composition further comprises at least one complexing agent effective for dissociating the at least one hydroxide compound in sufficient quantity to effect lanthionization of the keratinous fibers.

The present invention also provides a method for lanthionizing keratinous fibers to achieve relaxation of the keratinous fibers comprising generating hydroxide ions in at least one solvent, wherein the step of generating comprises at least one hydroxide compound and at least one oxidizing agent in the at least one solvent; applying a composition comprising the generated hydroxide ions to keratinous fibers for a sufficient period of time to relax at least one keratinous fiber; and heating the keratinous fibers. The at least one hydroxide compound and the at least one oxidizing agent are present in a combined amount effective to relax the keratinous fibers. The at least one hydroxide compound may be added to a composition containing the at least one oxidizing agent, or vice versa. In one embodiment, the heat-activated composition is applied prior to or during heating. In another embodiment, the heat-activated composition is applied prior to and during heating. The lanthionization is terminated when a desired level of relaxation of the keratinous fibers has been reached. In one embodiment, the composition further comprises a cation exchange composition. In another embodiment, the composition further comprises at least one complexing agent effective for dissociating the at least one hydroxide compound in sufficient quantity to effect lanthionization of the keratinous fibers.

According to the present invention, the at least one hydroxide compound may be chosen from any compound comprising at least one hydroxide group which may at least partially dissociate into a counterion and a hydroxide ion in solution. Non-limiting examples of the at least one hydroxide compound include alkali metal hydroxides, alkaline earth metal hydroxides, transition metal hydroxides, lanthanide metal hydroxides, actinide metal hydroxides, Group III hydroxides, Group IV hydroxides, Group V hydroxides, Group VI hydroxides, organic hydroxides, and compounds comprising at least one hydroxide substituent which is at least partially hydrolyzable. Other non-limiting examples of the at least one hydroxide compound include sodium hydroxide, potassium hydroxide, lithium hydroxide, rubidium hydroxide, cesium hydroxide, francium hydroxide, beryllium hydroxide, magnesium hydroxide, calcium hydroxide, strontium hydroxide, barium hydroxide, cupric hydroxide, molybdenum hydroxide, manganese hydroxide, zinc hydroxide, cobalt hydroxide, nickel hydroxide, cadmium hydroxide, gold hydroxide, lanthanum hydroxide, cerium hydroxide, actinium hydroxide, thorium hydroxide, aluminum hydroxide, guanidine hydroxides and quaternary ammonium hydroxides. The at least one hydroxide compound can also be chosen from those formed in situ, such as, for example, guanidine hydroxide. As previously mentioned, guanidine hydroxide may be formed in situ, for example, from the reaction of calcium hydroxide and guanidine carbonate.

According to the present invention, the at least one hydroxide compound is generally present in an amount sufficient to effect relaxation of the keratinous fibers without damaging the fibers. According to one embodiment of the present invention, the at least one hydroxide compound is present in an amount such that the amount of hydroxide ion generally ranges from 0.01% to 2.5% by weight relative to the total weight of the composition, such as from 0.01% to 2%, further such as from 0.01% to 1%, and further such as from 0.01% to 0.5%.

The at least one oxidizing agent of the present invention may be chosen from any oxidizing agents commonly used on keratinous fibers. The at least one oxidizing agent may be chosen from oxidizing agents such as, for example, those listed in the *International Cosmetic Ingredient Dictionary and Handbook* 8$^{th}$ Ed., Vol. 2 (2000) at pages 1763-1764. Non-limiting examples of the at least one oxidizing agent include hydrogen peroxide, urea peroxide, alkali metal bromates and persalts such as perborates and persulphates. In one embodiment, the at least one oxidizing agent is hydrogen peroxide.

According to the present invention, the at least one oxidizing agent and at least one hydroxide compound are present in a combined amount effective to relax the keratinous fibers. In one embodiment, the at least one oxidizing agent is present in an amount ranging from 1% to 12% by weight relative to the total weight of the composition, such as from 3% to 6% by weight. The aforementioned amounts were calculated based on hydrogen peroxide as the at least one oxidizing agent. One of skill in the art may adjust the amounts according to the particular at least one oxidizing agent chosen.

According to the present invention, the at least one solvent may be chosen from, for example, solvents commonly used in compositions for keratinous fibers. Non-limiting examples of the at least one solvent include water and solvents which may lower the ionic bonding forces in the solute molecules enough to cause at least partial separation of their constituent ions, such as dimethyl sulfoxide (DMSO). In one embodiment, the at least one solvent is chosen from water and DMSO. The at least one solvent can be present in an amount sufficient to ensure that, upon mixing, enough of the generated available hydroxide ions remain soluble in order to effect lanthionization of keratinous fibers.

In one embodiment, the compositions of the present invention as well as those used in the methods of the present invention may be in the form of an oil-in-water emulsion, a water-in-oil emulsion, a dispersion, a suspension, a cream, a foam, a gel, a spray, a powder or a liquid.

Further, the compositions of the present invention as well as those used in the methods of the present invention may further comprise at least one suitable additive chosen from additives commonly used in hair relaxing compositions. Non-limiting examples of the at least one suitable additive include dyes, anionic surfactants, cationic surfactants, nonionic surfactants, amphoteric surfactants, fragrances, screening agents, preserving agents, proteins, vitamins, silicones, polymers such as thickening polymers, plant oils, mineral oils, synthetic oils and any other additive conventionally used in compositions for the care and/or treatment of keratinous fibers.

Further, these compositions may further comprise at least one cation exchange composition which may be effective in participating in the lanthionizing process. In one embodiment, the at least one cation exchange composition is chosen from silicates. Non-limiting examples of silicates include aluminum silicates and silicates of alkali metals (such as analcime, chabazite, gmelinite, harmotome, levynite, mordenite, epistilbite, heulandite, natrolite, stilbite, edingtonite, mesolite, scolecite, thomosonite, brewsterite, faujasite, gismondine, laumontite, phillipsite, and aluminosilicate).

Non-limiting examples of alkali metals are sodium, lithium, potassium and mixtures of any of the foregoing. In one embodiment, the at least one cation exchange composition is a clay. In another silicates are chosen from zeolites, while in yet another embodiment, silicates are chosen from zeolite clays.

These compositions may further comprise at least one complexing agent effective for dissociating the at least one hydroxide compound in an amount sufficient to effect lanthionization of keratinous fibers. The at least one complexing agent may be an agent, such as a chelating agent or a sequestering agent, that leads to a partial or full dissociation of the at least one hydroxide compound. The at least one complexing agent may chelate, sequester or otherwise tie up the counter ion of the at least one hydroxide compound, allowing more available hydroxide ions to be liberated. Of course, the at least one complexing agent may do both. In any event, the net effect of the use of at least one complexing agent in accord with the present invention is the generation of enough available hydroxide ions to effect lanthionization of keratinous fibers without relying on precipitation of a counter ion, such as $Ca^{++}$ in the form of $CaCO_3$.

In a multicomponent kit, for example, the at least one oxidizing agent may be formulated with the component comprising at least one hydroxide compound or with the component comprising at least one complexing agent or itself may be a third component that is combined with one or both of the component comprising at least one hydroxide compound and the component comprising at least one complexing agent.

In one embodiment, the at least one complexing agent of the present invention may be chosen from chelating agents, sequestering agents and salts of any of the foregoing. A chelating agent is a compound or ligand that can bind to a metal ion, usually through more than one ligand atom, to form a chelate. See Lewis, R. J., *Hawley's Condensed Chemical Dictionary* p. 240 (1997). A chelate is usually a type of coordination compound in which a central metal ion, such as $Co^{2+}$, $Ni^{2+}$, $Cu^{2+}$, $Ca^{2+}$ or $Zn^{2+}$, is attached by coordinate links to two or more nonmetal atoms, i.e., ligands, in the same molecule. Non-limiting examples of common chelating agents include ethylene-diaminetetraacetic acid (EDTA), nitrilotriacetic acid and ethyleneglycol-bis(β-amino-ethyl ether)-N,N-tetraacetic acid.

Sequestering agents may be any material that prevents at least one ion from exhibiting its usual properties due to close combination with that material. Id. Certain phosphates, for example, form a coordination complex with metal ions in solution so that the usual precipitation reactions may be prevented. Id. For example, calcium soap precipitates are not produced from hard water treated with certain phosphates or metaphosphates. Id. Other non-limiting examples of sequestering agents include hydroxy carboxylic acids, such as gluconic acid, citric acid and tartaric acid. Id.

In addition, other non-limiting examples of chelating agents and sequestering agents include phosphonates, amino acids and crown ethers. In one embodiment, the at least one complexing agent is chosen from amino acids, such as monosodium glutamate, a known calcium chelator.

The at least one complexing agent may also be chosen from phosphates demonstrating chelating and/or sequestering properties, phosphonates demonstrating chelating and/or sequestering properties, and silicates demonstrating chelating and/or sequestering properties. Non-limiting examples of phosphates demonstrating chelating and/or sequestering properties include tripotassium phosphate and trisodium phosphate. Non-limiting examples of silicates demonstrating chelating and/or sequestering properties include disodium silicate and dipotassium silicate.

Further, the at least one complexing agent may also be chosen from organic acids and salts thereof. The cations that may be used to form the salts of organic acids of the present invention may be chosen from organic cations and inorganic cations. In one embodiment, the inorganic cations are chosen from potassium, sodium and lithium. In another embodiment, the at least one complexing agent is chosen from mono-hydroxycarboxylic acids, dihydroxycarboxylic acids, polyhydroxycarboxylic acids, mono-aminocarboxylic acids, di-aminocarboxylic acids, poly-aminocarboxylic acids, mono-hydroxysulfonic acids, di-hydroxysulfonic acids, polyhydroxysulfonic acids, mono-hydroxyphosphonic acids, dihydroxyphosphonic acids, polyhydroxyphosphonic acids, mono-aminophosphonic acids, diaminophosphonic acids and polyaminophosphonic acids.

In a further embodiment, the at least one complexing agent is chosen from ethylene diamine tetraacetic acid (EDTA), N-(hydroxyethyl) ethylene diamine triacetic acid, aminotrimethylene phosphonic acid, diethylenetriamine-pentaacetatic acid, lauroyl ethylene diamine triacetic acid, nitrilotriacetic acid, iminodisuccinic acid, tartaric acid, citric acid, N-2-hydroxyethyliminodiacetic acid and salts of any of the foregoing.

In yet another embodiment, the at least one complexing agent is chosen from a salt of EDTA, such as sodium EDTA, lithium EDTA, potassium EDTA and guanidine EDTA. EDTA has a strong calcium binding constant over a wide range of pH. For example, tetrasodium EDTA generally solubilizes calcium hydroxide in aqueous media to give a clear solution. The use of at least one complexing agent, such as tetrasodium EDTA, that solubilizes the counter ion of the at least one hydroxide compound may offer the benefit of no "ashing." However, the use of one or more complexing agents that do not completely solubilize the counter ion but only form slightly-soluble or sparingly-soluble complexing agent-counter ion complexes is also within the practice of the invention.

In another embodiment, the at least one complexing agent may comprise at least one "soft" entity chosen from "soft" bases and "soft" cations and at least one anion chosen from chelating anions and sequestering anions. Non-limiting examples of "soft" cations include organic cations such as guanidine. Non-limiting examples of "soft" bases include amines such as monoethanolamine, diethanolamine and triethanolamine. Such a combination of at least one "soft" entity and at least one anion may be effective if the "soft" entity exists at a high enough pH to achieve straightening or relaxing of the hair fibers. For example, amino acids such as arginine may be used to neutralize EDTA to make a "soft" base/strong chelator pair.

Depending on the nature of the at least one complexing agent, the solubility of the complex formed between the at least one complexing agent and the counter ion of the at least one hydroxide compound in the reaction medium may vary. In one embodiment, the at least one complexing agent-counter ion complex is considered by one of ordinary skill in the art to be soluble in the reaction medium. In another embodiment, a composition of the invention provides for an at least one complexing agent-counter ion complex having a solubility in water of greater than 0.03% at 25° C. and at a pH of 7.0, such as greater than 1% at 25° C. and at a pH of 7.0.

As one of ordinary skill in the art would recognize, mixtures of complexing agents including mixtures of at least one chelating agent and at least one sequestering agent are also within the practice of the invention. In one embodiment, a less active chelating agent, such as pentasodium aminotrimethylene phosphonate, may be mixed with a more active chelating agent, such as EDTA, to achieve a desired lanthionization of keratinous fibers at a slower rate.

The compositions of the present invention may be provided as one-part compositions comprising at least one hydroxide compound, at least one oxidizing agent, and, optionally, at least one cation exchange resin and/or at least one complexing agent. Alternatively, the compositions may be provided in the form of a multicompartment kit. According to one embodiment of the present invention, the multicompartment kit for lanthionizing keratinous fibers may comprise at least two separate compartments. A first compartment of the kit may comprise a first composition containing at least one hydroxide compound. This first composition can be in the form of an emulsion, suspension, solution, gel, cream, or paste. A second compartment of the kit can comprise at least one oxidizing agent, and, optionally, at least one complexing agent that is effective for dissociating the at least one hydroxide compound in sufficient quantity to effect lanthionization of keratinous fibers. This composition may be in the form of an emulsion, suspension, solution, gel, cream, or paste. The first and/or the second compartments may further contain at least one cation exchange composition. The skilled artisan, based on the stability of the composition and the application envisaged, will be able to determine how the composition and/or multicompartment compositions should be stored and mixed.

Other than in the operating example, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and in the attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. The following example is intended to illustrate the invention without limiting the scope as a result. The percentages are given on a weight basis.

EXAMPLE

Relaxing Efficiency of Naturally Kinky Hair Treated with NaOH/Hydrogen Peroxide

Compositions comprising from 0.01% to 0.5% NaOH (a hydroxide compound) and from 3% to 12% hydrogen peroxide (an oxidizing agent) were prepared as shown in Table 1 below. A naturally kinky hair swatch was either sprayed with, or was soaked in, the above solution and then blotted dry. A hot curling iron was used to pull the hair straight for 3-12 seconds. The hair swatch was rinsed and shampooed, and then placed in a humidity chamber at 90% Relative Humidity (% RH) for 24 hours. The percent Relaxing Efficiency (% RE) is defined as $$\% RE = (L_f/L_t) \times 100$$

where
$L_f$ = length of the relaxed hair after 24 hours at 90% RH
$L_t$ = length of the hair at the straight configuration The greater the relaxing efficiency (% RE), the straighter the hair after treatment.

The results are shown in Table 1.

TABLE 1

Relaxing Efficiency (% RE) of Hair Treated with Various Compositions After 24 hours under 90% Relative Humidity

| Amount of Hydrogen Peroxide (%) | Amount of NaOH (%) | | |
|---|---|---|---|
| | 0.01 | 0.2 | 0.5 |
| 1 | No significant relaxation | | |
| 3 | 22% | 30% | 29% |
| 6 | 50% | 49% | 48% |
| 12 | 89% | 94% | 96% |

A high relaxation efficiency after 24 hours under 90% relative humidity indicates that the hair did not display reversion. The data show that naturally kinky hair can be effectively relaxed without substantial reversion after being treated with solutions containing low concentrations of NaOH and hydrogen peroxide and then subjected to heat.

What is claimed is:

1. A composition for lanthionizing keratinous fibers to achieve relaxation of said keratinous fibers comprising:
   (i) at least one hydroxide compound;
   (ii) at least one oxidizing agent; and
   (iii) at least one complexing agent effective for dissociating the at least one hydroxide compound,
   wherein said at least one hydroxide compound and said at least one oxidizing agent are present in the composition in a sufficient quantity to effect lanthionization of keratinous fibers.

2. A composition according to claim 1, wherein said at least one hydroxide compound is chosen from alkali metal hydroxides, alkaline earth metal hydroxides, transition metal hydroxides, lanthanide metal hydroxides, actinide metal hydroxides, Group III hydroxides, Group IV hydroxides, Group V hydroxides, Group VI hydroxides, organic hydroxides, and compounds comprising at least one hydroxide substituent which is at least partially hydrolyzable.

3. A composition according to claim 2, wherein said at least one hydroxide compound is chosen from sodium hydroxide, lithium hydroxide, and potassium hydroxide.

4. A composition according to claim 3, wherein said at least one hydroxide compound is sodium hydroxide.

5. A composition according to claim 1, wherein said at least one hydroxide compound is present in an amount such that the amount of hydroxide ion ranges from 0.01% to 2.5% by weight relative to the total weight of said composition.

6. A composition according to claim 5, wherein said at least one hydroxide compound is present in an amount such that the amount of hydroxide ion ranges from 0.01% to 2% by weight relative to the total weight of said composition.

7. A composition according to claim 6, wherein said at least one hydroxide compound is present in an amount such that the amount of hydroxide ion ranges from 0.01% to 1% by weight relative to the total weight of said composition.

8. A composition according to claim 1, wherein said at least one hydroxide compound is present in an amount such that the amount of hydroxide ion ranges from 0.01% to 0.5% by weight relative to the total weight of said composition.

9. A composition according to claim 1, wherein said at least one oxidizing agent is chosen from hydrogen peroxide, urea peroxide, alkali metal bromates and persalts.

10. A composition according to claim 9, wherein said at least one oxidizing agent is chosen from hydrogen peroxide.

11. A composition according to claim 1, wherein said at least one oxidizing agent is present in an amount ranging from 1% to 12% by weight relative to the total weight of the composition.

12. A composition according to claim 11, wherein said at least one oxidizing agent is present in an amount ranging from 3% to 6% by weight relative to the total weight of the composition.

13. A composition according to claim 1, further comprising at least one cation exchange composition.

14. A composition according to claim 13, wherein said at least one cation exchange composition is chosen from clays.

15. A composition according to claim 13, wherein said at least one cation exchange composition is chosen from silicates.

16. A composition according to claim 15, wherein said silicates are chosen from analcime, chabazite, gmelinite, harmotome, levynite, mordenite, epistilbite, heulandite, natrolite, stilbite, edingtonite, mesolite, scolecite, thomosonite, brewsterite, faujasite, gismondine, laumontite, phillipsite, and aluminosilicate.

17. A composition according to claim 15, wherein said silicates are chosen from zeolites.

18. A composition according to claim 15, wherein said silicates are chosen from zeolite clays.

19. A composition according to claim 1, further comprising at least one solvent.

20. A composition according to claim 19, wherein said at least one solvent is chosen from DMSO and water.

21. A composition according to claim 1, wherein said at least one complexing agent is chosen from chelating agents, sequestering agents and salts of any of the foregoing.

22. A composition according to claim 1, wherein said dissociation is chosen from partial dissociation and full dissociation.

23. A composition according to claim 1, wherein at least one entity chosen from said least one hydroxide compound and said at least one complexing agent is formulated with at least one oxidizing agent.

24. A composition according to claim 21, wherein said chelating agents are chosen from ethylene-diaminetetraacetic acid (EDTA), nitrilotriacetic acid and ethyleneglycol-bis(-amino-ethyl ether)-N,N-tetraacetic acid.

25. A composition according to claim 21, wherein said sequestering agents are chosen from hydroxy carboxylic acids.

26. A composition according to claim 25, wherein said hydroxyl carboxylic acids are chosen from gluconic acid, citric acid and tartaric acid.

27. A composition according to claim 21, wherein said at least one complexing agent is chosen from amino acids and crown ethers.

28. A composition according to claim 27, wherein said amino acids are monosodium glutamate.

29. A composition according to claim 21, wherein said at least one complexing agent is chosen from phosphates demonstrating chelating properties, phosphates demonstrating sequestering properties, phosphonates demonstrating chelating properties, phosphonates demonstrating sequestering properties, silicates demonstrating chelating properties and silicates demonstrating sequestering properties.

30. A composition according to claim 29, wherein said at least one complexing agent is chosen from tripotassium phosphate and trisodium phosphate.

31. A composition according to claim 29, wherein said at least one complexing agent is chosen from disodium silicate and dipotassium silicate.

32. A composition according to claim 1, wherein said at least one complexing agent is chosen from organic acids and salts thereof.

33. A composition according to claim 1, wherein said at least one complexing agent is chosen from mono-hydroxycarboxylic acids, dihydroxycarboxylic acids, polyhydroxycarboxylic acids, mono-aminocarboxylic acids, di-aminocarboxylic acids, poly-aminocarboxylic acids, mono-hydroxysulfonic acids, di-hydroxysulfonic acids, polyhydroxysulfonic acids, mono-hydroxyphosphonic acids, dihydroxyphosphonic acids, polyhydroxyphosphonic acids, mono-aminophosphonic acids, diaminophosphonic acids and polyaminophosphonic acids.

34. A composition according to claim 1, wherein said at least one complexing agent is chosen from ethylene diamine tetraacetic acid (EDTA), N-(hydroxyethyl) ethylene diamine triacetic acid, aminotrimethylene phosphonic acid, diethylenetriamine-pentaacetatic acid, lauroyl ethylene diamine triacetic acid, nitrilotriacetic acid, iminodisuccinic acid, tartaric acid, citric acid, N-2-hydroxyethyliminodiacetic acid and salts of any of the foregoing.

35. A composition according to claim 34, wherein said at least one complexing agent is chosen from sodium EDTA, lithium EDTA, potassium EDTA and guanidine EDTA.

36. A composition according to claim 1, wherein said at least one complexing agent and said at least one hydroxide compound form at least one complexing agent-counter ion complex.

37. A composition according to claim 36, wherein said composition comprises at least two complexing agents.

38. A composition according to claim 1, further comprising at least one additive chosen from dyes, anionic surfactants, cationic surfactants, nonionic surfactants, amphoteric surfactants, fragrances, silicones, silicone derivatives, screening agents, preserving agents, proteins, vitamins, polymers, plant oils, mineral oils and synthetic oils.

39. A composition according to claim 1, wherein said composition is in the form of an oil-in-water emulsion, a water-in-oil emulsion, a dispersion, a suspension, a cream, a foam, a gel, a spray, a powder or a liquid.

40. A composition according to claim 1, wherein said keratinous fibers are chosen from hair.

41. A composition according to claim 1, wherein said composition is heat-activated.

42. A composition for lanthionizing keratinous fibers to achieve relaxation of said keratinous fibers comprising:
    (i) at least one hydroxide compound;
    (ii) at least one oxidizing agent, and
    (iii) at least one complexing agent effective for dissociating the at least one hydroxide compound,
    wherein said at least one hydroxide compound and said at least one oxidizing agent are present in the composition in a sufficient quantity to effect lanthionization of keratinous fibers,
    and further wherein said at least one hydroxide compound is present in an amount such that the amount of hydroxide ion ranges from 0.01% to 2% by weight relative to the total weight of the composition.

43. A composition for lanthionizing keratinous fibers to achieve relaxation of said keratinous fibers comprising:
    (i) at least one hydroxide compound; and (ii) at least one oxidizing agent; and
(iii) at least one complexing agent effective for dissociating the at least one hydroxide compound,
wherein said at least one hydroxide compound and said at least one oxidizing agent are present in the composition in a sufficient quantity to effect lanthionization of keratinous fibers,
and further wherein said at least one hydroxide compound is present in an amount such that the amount of hydroxide ion ranges from 0.01% to 1% by weight relative to the total weight of said composition.

44. A composition for lanthionizing keratinous fibers to achieve relaxation of said keratinous fibers comprising:

(i) at least one hydroxide compound; and
(ii) at least one oxidizing agent; and
(iii) at least one complexing agent effective for dissociating the at least one hydroxide compound,
wherein said at least one hydroxide compound and said at least one oxidizing agent are present in the composition in a sufficient quantity to effect lanthionization of keratinous fibers
and further wherein said at least one hydroxide compound is present in an amount such that the amount of hydroxide ion ranges from 0.01% to 0.5% by weight relative to the total weight of said composition.

* * * * *